(12) United States Patent
Freitag

(10) Patent No.: US 7,487,778 B2
(45) Date of Patent: Feb. 10, 2009

(54) TRACHEAL CATHETER AND PROSTHESIS AND METHOD OF RESPIRATORY SUPPORT OF A PATIENT

(75) Inventor: Lutz Freitag, Hemer (DE)

(73) Assignee: Breathe Technologies, Inc., Fremont, CA (US)

( * ) Notice: Subject to any disclaimer, the term of this patent is extended or adjusted under 35 U.S.C. 154(b) by 533 days.

(21) Appl. No.: 10/771,803

(22) Filed: Feb. 4, 2004

(65) Prior Publication Data
US 2005/0034721 A1  Feb. 17, 2005

(30) Foreign Application Priority Data
Aug. 11, 2003  (DE) ................. 103 37 138

(51) Int. Cl.
*A62B 9/00* (2006.01)
(52) U.S. Cl. .............. 128/207.14; 128/207.16
(58) Field of Classification Search ........... 128/200.26, 128/207.14, 207.15, 207.16, 207.24, 204.18, 128/204.23; 623/9; 604/99.01, 102.01, 103.01
See application file for complete search history.

(56) References Cited

U.S. PATENT DOCUMENTS

| | | | |
|---|---|---|---|
| 3,267,935 A | 8/1966 | Andreasen et al. | |
| 3,357,427 A | 12/1967 | Schreiber | |
| 3,493,703 A | 2/1970 | Finan | |
| 3,610,247 A | 10/1971 | Jackson | |
| 3,721,233 A * | 3/1973 | Montgomery et al. | 128/207.14 |
| 3,741,208 A | 6/1973 | Jonsson et al. | |
| 3,794,026 A | 2/1974 | Jacobs | |
| 3,961,627 A | 6/1976 | Ernst et al. | |
| 3,991,790 A | 11/1976 | Russell | |
| 4,003,377 A | 1/1977 | Dahl | |
| 4,067,328 A | 1/1978 | Manley | |

(Continued)

FOREIGN PATENT DOCUMENTS

CA  2535450  2/2005

(Continued)

OTHER PUBLICATIONS

Haenel, et al., "Efficacy of Selective Intrabronchial Air Insufflation in Acute Lobar Colapse," *Am J Surg*, 1992, vol. 164, No. 5, pp. 501-505.

(Continued)

*Primary Examiner*—Steven O Douglas
(74) *Attorney, Agent, or Firm*—Michele Van Patten Frank; Patton Boggs LLP

(57) ABSTRACT

A method and apparatus is described for supporting the respiration of a patient. The spontaneous respiration of a patient can be detected by sensors and during inhalation an additional amount of oxygen can be administered to the lungs via a jet gas current. If required, during exhalation a countercurrent can be administered to avoid collapse of the respiration paths. This therapy can be realized by an apparatus including a transtracheal catheter, an oxygen pump connected to an oxygen source, spontaneous respiration sensor(s) connected to a control unit for activating the oxygen pump and, if needed, a tracheal prosthesis. The tracheal prosthesis may include a connection for the catheter and the breath sensor(s). The tracheal prosthesis, if used, and the catheter can be dimensioned so the patient can freely breathe, cough, swallow and speak without restriction, and the system can be wearable to promote mobility.

39 Claims, 4 Drawing Sheets

U.S. PATENT DOCUMENTS

| | | | |
|---|---|---|---|
| 4,231,365 A | 11/1980 | Scarberry | |
| 4,261,355 A | 4/1981 | Glazener | |
| 4,265,237 A | 5/1981 | Schwanbom et al. | |
| 4,274,162 A | 6/1981 | Joy et al. | |
| 4,413,514 A | 11/1983 | Bowman | |
| 4,449,523 A | 5/1984 | Szachowicz et al. | |
| 4,481,944 A | 11/1984 | Bunnell | |
| 4,488,548 A | 12/1984 | Agdanowski | |
| 4,506,667 A | 3/1985 | Ansite | |
| 4,527,557 A | 7/1985 | DeVries et al. | |
| 4,535,766 A | 8/1985 | Baum et al. | |
| 4,537,188 A | 8/1985 | Phuc | |
| 4,630,606 A | 12/1986 | Weerda et al. | |
| 4,644,947 A * | 2/1987 | Whitwam et al. | 128/204.25 |
| 4,744,356 A | 5/1988 | Greenwood | |
| 4,747,403 A | 5/1988 | Gluck et al. | |
| 4,773,411 A | 9/1988 | Downs | |
| 4,813,431 A | 3/1989 | Brown | |
| 4,825,859 A | 5/1989 | Lambert | |
| 4,832,014 A | 5/1989 | Perkins | |
| 4,838,255 A | 6/1989 | Lambert | |
| 4,850,350 A | 7/1989 | Jackson | |
| 4,905,688 A | 3/1990 | Vicenzi et al. | |
| 4,938,212 A | 7/1990 | Snook et al. | |
| 4,967,743 A | 11/1990 | Lambert | |
| 5,000,175 A | 3/1991 | Pue | |
| 5,002,050 A | 3/1991 | McGinnis | |
| 5,022,394 A | 6/1991 | Chmielinski | |
| 5,024,219 A | 6/1991 | Dietz | |
| 5,038,771 A | 8/1991 | Dietz | |
| 5,048,515 A | 9/1991 | Sanso | |
| 5,054,484 A * | 10/1991 | Hebeler, Jr. | 128/207.16 |
| 5,058,580 A | 10/1991 | Hazard | |
| 5,090,408 A | 2/1992 | Spofford et al. | |
| 5,101,820 A | 4/1992 | Christopher | |
| 5,134,995 A | 8/1992 | Gruenke et al. | |
| 5,134,996 A | 8/1992 | Bell | |
| 5,148,802 A | 9/1992 | Sanders et al. | |
| 5,161,525 A | 11/1992 | Kimm et al. | |
| 5,181,509 A | 1/1993 | Spofford et al. | |
| 5,184,610 A | 2/1993 | Marten et al. | |
| 5,186,167 A | 2/1993 | Kolobow | |
| 5,193,533 A | 3/1993 | Body et al. | |
| 5,217,008 A | 6/1993 | Lindholm | |
| 5,233,979 A | 8/1993 | Strickland | |
| 5,239,994 A | 8/1993 | Atkins | |
| 5,243,972 A | 9/1993 | Huang | |
| 5,255,675 A | 10/1993 | Kolobow | |
| 5,258,027 A | 11/1993 | Berghaus | |
| 5,271,388 A | 12/1993 | Whitwam et al. | |
| 5,279,288 A | 1/1994 | Christopher | |
| 5,287,852 A | 2/1994 | Arkinstall | |
| 5,303,700 A | 4/1994 | Weismann et al. | |
| 5,331,995 A | 7/1994 | Westfall et al. | |
| 5,339,809 A | 8/1994 | Beck, Jr. et al. | |
| 5,400,778 A | 3/1995 | Jonson et al. | |
| 5,419,314 A | 5/1995 | Christopher | |
| 5,438,980 A | 8/1995 | Phillips | |
| 5,460,613 A | 10/1995 | Ulrich et al. | |
| 5,474,062 A | 12/1995 | DeVires et al. | |
| 5,485,850 A | 1/1996 | Dietz | |
| 5,507,282 A | 4/1996 | Younes et al. | |
| 5,513,628 A | 5/1996 | Coles et al. | |
| 5,535,738 A | 7/1996 | Estes et al. | |
| 5,542,415 A | 8/1996 | Brody | |
| 5,546,935 A | 8/1996 | Champeau | |
| 5,549,106 A | 8/1996 | Gruenke et al. | |
| 5,558,086 A | 9/1996 | Smith et al. | |
| 5,598,840 A | 2/1997 | Iund et al. | |
| 5,669,380 A | 9/1997 | Garry et al. | |
| 5,687,714 A | 11/1997 | Kolobow et al. | |
| 5,690,097 A | 11/1997 | Howard et al. | |
| 5,715,812 A | 2/1998 | Deighan et al. | |
| 5,715,815 A | 2/1998 | Lorenzen et al. | |
| 5,720,278 A | 2/1998 | Lachmann et al. | |
| 5,735,268 A | 4/1998 | Chua et al. | |
| 5,740,796 A | 4/1998 | Skog | |
| 5,762,638 A | 6/1998 | Shikani et al. | |
| 5,791,337 A | 8/1998 | Coles et al. | |
| 5,819,723 A | 10/1998 | Joseph | |
| 5,865,173 A | 2/1999 | Froehlich | |
| 5,904,648 A | 5/1999 | Arndt et al. | |
| 5,906,204 A | 5/1999 | Beran et al. | |
| 5,911,756 A | 6/1999 | Debry | |
| 5,918,597 A | 7/1999 | Jones et al. | |
| 5,931,162 A | 8/1999 | Christian | |
| 5,937,853 A * | 8/1999 | Strom | 128/204.23 |
| 5,954,050 A * | 9/1999 | Christopher | 128/204.23 |
| 5,964,223 A | 10/1999 | Baran | |
| 5,975,077 A | 11/1999 | Hofstetter et al. | |
| 5,975,081 A | 11/1999 | Hood et al. | |
| 6,039,696 A | 3/2000 | Bell | |
| 6,105,575 A | 8/2000 | Estes et al. | |
| 6,109,264 A | 8/2000 | Sauer | |
| 6,152,132 A | 11/2000 | Psaros | |
| 6,213,119 B1 | 4/2001 | Brydon et al. | |
| 6,220,244 B1 | 4/2001 | McLaughlin | |
| 6,227,200 B1 | 5/2001 | Crump et al. | |
| 6,305,374 B1 | 10/2001 | Zdrojkowski et al. | |
| 6,315,739 B1 | 11/2001 | Merilainen et al. | |
| 6,345,619 B1 | 2/2002 | Finn | |
| 6,357,438 B1 | 3/2002 | Hansen | |
| 6,378,520 B1 | 4/2002 | Davenport | |
| 6,427,690 B1 | 8/2002 | McCombs et al. | |
| 6,439,228 B1 | 8/2002 | Hete et al. | |
| 6,450,164 B1 | 9/2002 | Banner et al. | |
| 6,457,472 B1 | 10/2002 | Schwartz et al. | |
| 6,520,176 B1 | 2/2003 | Dubois et al. | |
| 6,520,183 B2 | 2/2003 | Amar | |
| 6,532,960 B1 * | 3/2003 | Yurko | 128/204.26 |
| 6,568,391 B1 | 5/2003 | Tatarek et al. | |
| 6,571,796 B2 | 6/2003 | Banner et al. | |
| 6,575,944 B1 | 6/2003 | McNary et al. | |
| 6,588,422 B1 | 7/2003 | Berthon-Jones et al. | |
| 6,609,517 B1 | 8/2003 | Estes et al. | |
| 6,626,175 B2 | 9/2003 | Jafari et al. | |
| 6,629,529 B2 | 9/2003 | Arnott | |
| 6,629,527 B1 | 10/2003 | Estes et al. | |
| 6,640,806 B2 | 11/2003 | Yurko | |
| 6,655,382 B1 | 12/2003 | Kolobow | |
| 6,666,208 B1 | 12/2003 | Schumacher et al. | |
| 6,668,829 B2 | 12/2003 | Biondi et al. | |
| 6,694,978 B1 * | 2/2004 | Bennarsten | 128/204.21 |
| 6,705,314 B1 | 3/2004 | O'Dea | |
| 6,722,360 B2 | 4/2004 | Doshi | |
| 6,722,362 B2 | 4/2004 | Hete et al. | |
| 6,752,151 B2 | 6/2004 | Hill | |
| 6,758,217 B1 | 7/2004 | Younes et al. | |
| 6,810,876 B2 | 11/2004 | Berthon-Jones | |
| 6,814,073 B2 | 11/2004 | Wickham | |
| 6,814,077 B1 | 11/2004 | Eistert | |
| 6,823,866 B2 | 11/2004 | Jafari et al. | |
| 6,840,240 B1 | 1/2005 | Berthon-Jones et al. | |
| 6,854,462 B2 | 2/2005 | Berthon-Jones et al. | |
| 6,877,511 B2 | 4/2005 | DeVries et al. | |
| 6,910,480 B1 | 6/2005 | Berthon-Jones | |
| 6,910,482 B2 | 6/2005 | Bliss et al. | |
| 6,913,601 B2 | 7/2005 | St. Goar et al. | |
| 6,915,803 B2 | 7/2005 | Berthon-Jones et al. | |
| 6,920,878 B2 | 7/2005 | Sinderby et al. | |
| 6,932,084 B2 | 8/2005 | Estes et al. | |
| 6,941,950 B2 | 9/2005 | Wilson et al. | |
| 6,948,497 B2 | 9/2005 | Zdrojkowski et al. | |
| 6,951,217 B2 | 10/2005 | Berthon-Jones | |

| | | |
|---|---|---|
| 6,971,382 B1 | 12/2005 | Corso |
| 6,997,881 B2 | 2/2006 | Green et al. |
| 7,000,612 B2 | 2/2006 | Jafari et al. |
| 7,011,091 B2 | 3/2006 | Hill et al. |
| 7,017,574 B2 | 3/2006 | Biondi et al. |
| 7,044,129 B1 | 5/2006 | Truschel et al. |
| 7,066,173 B2 | 6/2006 | Banner et al. |
| 7,077,132 B2 | 7/2006 | Berthon-Jones |
| 7,080,646 B2 | 7/2006 | Wiesmann et al. |
| 7,100,607 B2 | 9/2006 | Zdrojkowski et al. |
| 7,121,277 B2 | 10/2006 | Ström |
| 7,152,598 B2 | 12/2006 | Morris et al. |
| 7,156,090 B2 * | 1/2007 | Nomori ............. 128/200.26 |
| 7,195,016 B2 | 3/2007 | Loyd et al. |
| 7,222,623 B2 | 5/2007 | DeVries et al. |
| 7,255,103 B2 | 8/2007 | Bassin |
| 7,267,122 B2 | 9/2007 | Hill |
| 7,270,128 B2 | 9/2007 | Berthon-Jones et al. |
| 7,296,573 B2 | 11/2007 | Estes et al. |
| 7,373,939 B1 | 5/2008 | DuBois et al. |
| 2001/0035182 A1 | 11/2001 | Christopher |
| 2002/0179090 A1 | 12/2002 | Boussignac |
| 2003/0121519 A1 | 7/2003 | Estes et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2004/0040560 A1 | 3/2004 | Euliano et al. |
| 2004/0221848 A1 | 11/2004 | Hill |
| 2004/0221854 A1 | 11/2004 | Hete et al. |
| 2004/0231674 A1 | 11/2004 | Tanaka |
| 2004/0237963 A1 | 12/2004 | Berthon-Jones |
| 2004/0255943 A1 | 12/2004 | Morris et al. |
| 2005/0005936 A1 | 1/2005 | Wondka |
| 2005/0005938 A1 | 1/2005 | Berthon-Jones et al. |
| 2005/0034721 A1 | 2/2005 | Freitag |
| 2005/0034724 A1 | 2/2005 | O'Dea |
| 2005/0061322 A1 | 3/2005 | Freitag |
| 2005/0087190 A1 | 4/2005 | Jafari et al. |
| 2005/0098179 A1 | 5/2005 | Burton et al. |
| 2005/0121033 A1 | 6/2005 | Starr et al. |
| 2005/0121038 A1 | 6/2005 | Christopher |
| 2005/0166924 A1 | 8/2005 | Thomas et al. |
| 2005/0247308 A1 | 11/2005 | Frye et al. |
| 2006/0005834 A1 | 1/2006 | Aylsworth et al. |
| 2006/0096596 A1 | 5/2006 | Occhialini et al. |
| 2006/0124134 A1 | 6/2006 | Wood |
| 2006/0149144 A1 | 7/2006 | Lynn et al. |
| 2006/0150972 A1 | 7/2006 | Mizuta et al. |
| 2006/0201504 A1 | 9/2006 | Singhal et al. |
| 2006/0243278 A1 | 11/2006 | Hamilton et al. |
| 2008/0011298 A1 | 1/2008 | Mazar et al. |

FOREIGN PATENT DOCUMENTS

| | | |
|---|---|---|
| CN | 200480029872 | 11/2006 |
| DE | 19626924 | 1/1998 |
| DE | 10337138.9 | 3/2005 |
| EP | 0125424 | 11/1984 |
| EP | 0692273 | 1/1996 |
| EP | 0778035 | 6/1997 |
| EP | 1654023 | 5/2006 |
| IN | 317/KOLNP/06 | 3/2007 |
| JP | 2002-204830 | 7/2002 |
| JP | 2006/522883 | 2/2007 |
| WO | WO-98/01176 | 1/1998 |
| WO | WO-0176655 | 10/2001 |
| WO | WO-2005014091 | 2/2005 |
| WO | PCT-US06036600 | 8/2006 |
| WO | PCT-US07-017400 | 3/2007 |
| WO | WO-2007035804 | 3/2007 |
| WO | WO-2007/142812 | 12/2007 |

OTHER PUBLICATIONS

"AARC Clinical Practice Guideline: Oxygen Therapy in the Home or Extended Care Facility," *Respir Care*, 1992, vol. 37, No. 8, pp. 918-922.

MacIntyre, N. R., "Long-Term Oxygen Therapy: Conference Summary," *Resp Care*, 2000, vol. 45, No. 2, pp. 237-245.

*VHA/DOD Clinical Practice Guideline*, "Management of Chronic Obstructive Pulmonary Disease," Ver. 1.1a, Aug. 1999, Updated Nov. 1999.

Blanch, L. L., "Clinical Studies of Tracheal Gas Insufflation," *Respir Care*, 2001, vol. 45, No. 2, pp. 158-166.

Gregoretti, et al., "Transtracheal Open Ventilation in Acute Respiratory Failure Secondary to Severe Chronic Obstructive Pulmonary Disease Exacerbation," *Am J Respir Crit Care Med*, 2006, vol. 173, No. 8, pp. 877-881.

Christopher, et al., "Preliminary Observations of Transtracheal Augmented Ventilation for Chronic Severe Respiratory Disease," *Respir Care*, 2001, vol. 46, No. 1, pp. 15-25.

Chang, et al., "Reduced Inspiratory Muscle endurance Following Successful Weaning From Prolonged Mechanical Ventilation," *Chest*, 2005, vol. 128, No. 2, pp. 539-559.

Gaughan, et al., "A Comparison in a Lung Model of Low- and High-Flow Regulators for Transtracheal Jet Ventilation," *Anesthesiology*, 1992, vol. 77, No. 1, pp. 189-199.

Menon, et al., "Tracheal Perforation. A Complication Associated with Transtracheal Oxygen Therapy," *Chest*, 1993, vol. 104, No. 2, pp. 636-637.

Rothe, et al., "Near Fatal Complication of Transtracheal Oxygen Therapy with the SCOOP(R) System," *Pneumologie*, 1996, vol. 50, No. 10, pp. 700-702. (English Abstract provided).

International Search Report and Opinion for Application No. PCT/US07/17400, dated Apr. 28, 2008.

Ambrosino, "Weaning and Respiratory Muscle Dysfunction: The Egg Chicken Dilemma," Chest, 2005, vol. 128(2), pp. 481-483.

Messinger et al., "Using Tracheal Pressure to Trigger the Ventilator and Control Airway Pressure During Continuous Positive Airway Pressure Decreases Work of Breathing," Chest, 1995, vol. 108, No. 2, pp. 509-514.

Messinger et al., "Tracheal pressure triggering a demand flow CPAP system decreases work of breathing," Anesthesiology, 1994, vol 81, A272.

Koska et al., "Evaluation of a fiberoptic system for airway pressure monitoring," J. Clin Monit, 1993, vol. 10, No. 4, pp. 247-250.

Banner et al., "Imposed work of breathing and methods of triggering demand-flow, continuous positive airway pressure system," Critical Care Medicine, 1993, vol. 21, No. 2, pp. 183-190.

Banner et al., "Site of pressure measurement during spontaneous breathing with continuous positive airway pressure: Effect on calculating imposed work of breathing," Critical Care, 1992, vol. 20, No. 4, pp. 528-533.

Sinderby et al., "Neural control of mechanical ventilation in respiratory failure", Nat Med., 1999; 5:1433-1436.

Tiep et al., "Pulsed nasal and transtracheal oxygen delivery," Chest, 2001, vol. 97, pp. 364-368.

Yaeger et al., "Oxygen Therapy Using Pulse and Continuous Flow With a Transtracheal Catheter and a Nasal Cannula," Chest, 1994, vol. 106, pp. 854-860.

Passy-Muir Inc., "Clinical Inservice Outline", Apr. 2004, 19 pages.

Charlotte Regional Medical Center, "Application of the Passy-Muir Tracheostomy and Ventilator", Speech-Language Pathology Department, Jan. 1995, 8 pages.

"Passy-Muir Speaking Valves," Respiratory, Nov. 13, 1998, 7 pages.

Prigent et al., "Comparative Effeccts of Two Ventilatory Modes on Speech in Tracheostomized Patients with Neuromuscular Disease," *Am J Respir Crit Care Med*, 2003, vol. 167, No. 8, pp. 114-119.

International Search Report and Written Opinion for PCT/US07/12108, issued Aug. 8, 2008.

Co-pending U.S. Appl. No. 11/523,519, filed Sep. 20, 2006, Freitag.

Co-pending U.S. Appl. No. 10/567,746, filed Sep. 10, 2007, Freitag.

Co-pending U.S. Appl. No. 11/523,518, filed Sep. 20, 2006, Freitag et al.

Co-pending U.S. Appl. No. 11/798,965, filed May 18, 2007, Lutz Freitag.

Co-pending U.S. Appl. No. 11/882,530, filed Aug. 3, 2007, Lutz Freitag.

Co-pending U.S. Appl. No. 10/870,849, filed Jan. 13, 2005, Anthony Wondka.

European Patent Office Search Report issued Oct. 19, 2007.

Co-pending U.S. Appl. No. 60/924,514, filed May 18, 2007, Wondka et al.

Co-pending U.S. Appl. No. 60/960,370, filed Sep. 26, 2007, Wondka et al.

Co-pending U.S. Appl. No. 60/690,362, filed Sep. 26, 2007, Wondka et al.

International Search Report for Wo 2005/014091 (Application No. PCT/DE04/1646), dated Jan. 17, 2005.

Christopher, et al., "Transtracheal Oxygen Therapy for Refractory Hypoxemia," *JAMA*, 1986, vol. 256, No. 4, pp. 494-497.

Fink, J.B., "Helium-Oxygen: An Old Therapy Creates New Interest," *J Resp Care Pract now RT for Decision Makers in Respiratory Care*, Apr. 1999, pp. 71-76.

* cited by examiner

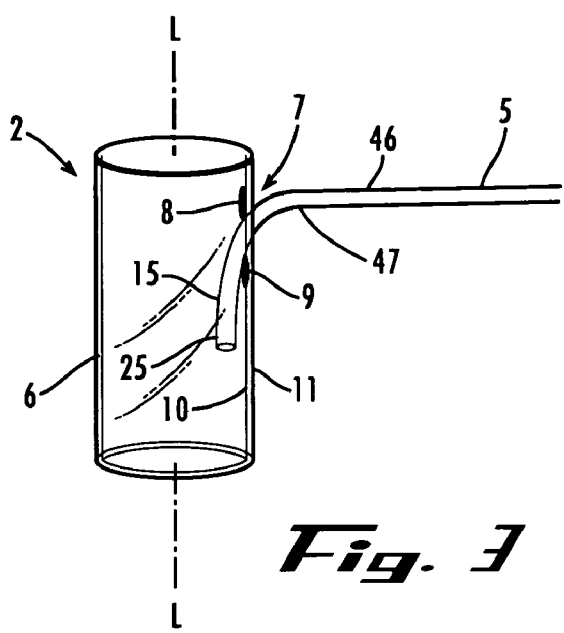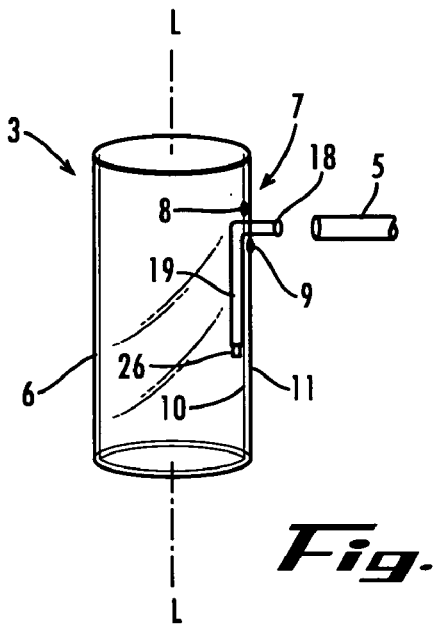
Fig. 3
Fig. 4
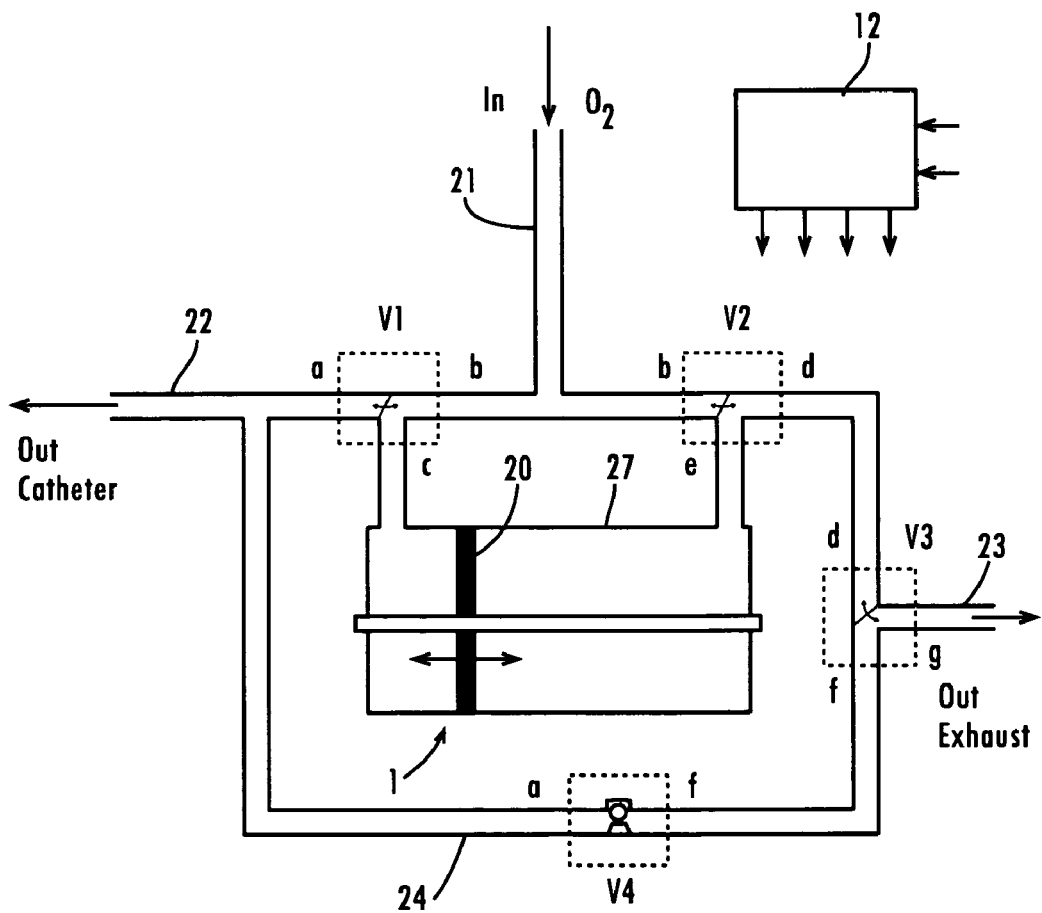
Fig. 5

TRACHEAL CATHETER AND PROSTHESIS AND METHOD OF RESPIRATORY SUPPORT OF A PATIENT

PRIORITY CLAIM

This patent application claims the benefit of priority under 35 U.S.C § 119 to co-pending German Patent Application Serial No. 10337138.9, filed Aug. 11, 2003.

FIELD OF INVENTION

The present invention relates generally to respiratory systems directed and more particularly to specialized mechanisms for enhanced ventilation of a patient.

BACKGROUND OF THE INVENTION

In order that the body can take in oxygen and give off carbon dioxide, both components of the respiratory bronchial system must function—the lungs as a gas-exchanging organ and the respiratory pump as a ventilation organ that transports air into the lungs and back out again. The breathing center in the brain, central and peripheral nerves, the osseous thorax and the breathing musculature as well as free, stable respiratory paths are necessary for a correct functioning of the respiratory pump.

In certain diseases there is a constant overload on or exhaustion of the respiratory pump. A typical syndrome is pulmonary emphysema with flat-standing diaphragms without the ability to contract. In the case of pulmonary emphysema the respiratory paths are usually extremely slack and tend to collapse. As a consequence of the flattened, over-extended diaphragms the patient cannot inhale deep enough. In addition, the patient cannot exhale sufficiently on account of the collapsing respiratory paths. This results in an insufficient respiration with an undersupply of oxygen and a rise of carbon dioxide in the blood, the so-called ventilatory insufficiency.

The treatment for inhalation difficulty often makes use of a breathing device. The so-called home respiration is an artificial respiration for supporting or completely relieving the respiratory pump.

The respiration can take place non-invasively via a tube and a nose mask or mouth mask that the patient can put on and take off as needed. However, this prevents the patient from breathing freely and speaking freely. In addition, a blocked tracheal cannula can be inserted into the trachea. This also has the consequence that the patient can no longer speak.

In the case of invasive respiration this usually occurs via a tracheostomy. This involves an opening placed in the trachea by an operation. A catheter about the diameter of a finger with a blocking balloon is inserted via the opening into the trachea and connected to a breathing apparatus. This makes a sufficiently deep respiration possible but prevents the patient from speaking. In addition to the respiration there is the transtracheal administration of oxygen via thinner catheters. U.S. Pat. No. 5,181,509 or 5,279,288 disclose corresponding embodiments. In this manner a highly dosed administration of oxygen is administered to the patient in a continuous stream with a permanently adjusted frequency. The flow of oxygen is regulated manually by a throttle device. However, simulation of the natural breathing process of a patient is not achieved because breathing is not deep enough. Also, the catheter end introduced into the trachea can result in irritations and a local traumatizing of the surrounding tissue in that it strikes against the trachea as a consequence of the respiratory movement or in that the surrounding tissue is dried out by the jet stream.

Furthermore, so-called "Montgomery T-tubes" are known that are inserted into the trachea. The patient can obtain oxygen via the shank of the T-piece run to the outside. In addition, the patient can draw off secretions himself if needed. The patient can breathe freely and speak when the front shank is closed; however, respiration is not possible via the Montgomery T-tube since the introduced air escapes upward into the buccal cavity or the pharyngeal area. An additional limitation of the above-referenced therapies is the impaired mobility of the patient because of inadequate ventilation as well as the bulk of the apparatus.

Therefore, there is an existing need for a respiratory system that provides a more efficient method for supporting the respiration of a patient and of creating an apparatus to this end that can also be taken along by the patient and is reliable in its use. Moreover, the there is a need for a tracheal prosthesis and a catheter that make possible a respiratory support synchronized with the spontaneous respiration of the patient without adversely affecting the patient's ability to speak.

SUMMARY OF EXEMPLARY EMBODIMENTS

It is a principal objective of the present invention to provide an apparatus and method that improves the quality of life of patients that require respiratory support. In the furtherance of this and other objectives, the present inventor provides a respiratory system that provides a more efficient method of supporting the respiration of a patient by providing additional oxygen when needed.

I is an additional objective in accordance with the present invention to provide as system that is portable and reliable in its use.

Yet another objective in accordance with the present invention is to provide a tracheal prosthesis and a catheter that make possible a respiratory support synchronized with the spontaneous respiration of the patient without adversely affecting the patient's ability to speak.

Further objectives, features and advantages of the invention will be apparent from the following detailed description taken in conjunction with the accompanying drawings.

BRIEF DESCRIPTION OF THE FIGURES

FIG. 3 shows a technically simplified view of a tracheal prosthesis in accordance with the invention.

FIG. 4 shows another embodiment of a tracheal prosthesis.

FIG. 5 shows, also in a scheme, an oxygen pump belonging to the apparatus of the invention showing the conduction of air and a control unit.

DETAILED DESCRIPTION OF AN EMBODIMENT

The present invention, in a preferred embodiment, provides an apparatus for supporting the respiration of a patient and to a tracheal prosthesis. According to the invention the spontaneous respiration of a patient is detected by sensors and at the end of an inhalation procedure an additional amount of oxygen is administered to the lungs via a jet gas current. This improves the absorption of oxygen during inhalation. If required, the exhalation procedure of the patient can be arrested or slowed by a countercurrent in order to avoid a collapse of the respiration paths in this manner. This procedure is realized by an apparatus comprising an oxygen pump that can be connected to an oxygen source and comprising a tracheal prosthesis that can be connected via a catheter. The spontaneous respiration of the patient is detected by sensors connected to a control unit for activating the oxygen pump. The tracheal prosthesis comprises a tubular support body with a connection for the catheter and two of the sensors are associated with the support body. The tracheal prosthesis and the jet catheter that is integrated or can be introduced are dimensioned in such a manner that the patient can freely breath and speak without restriction.

Figure 1:
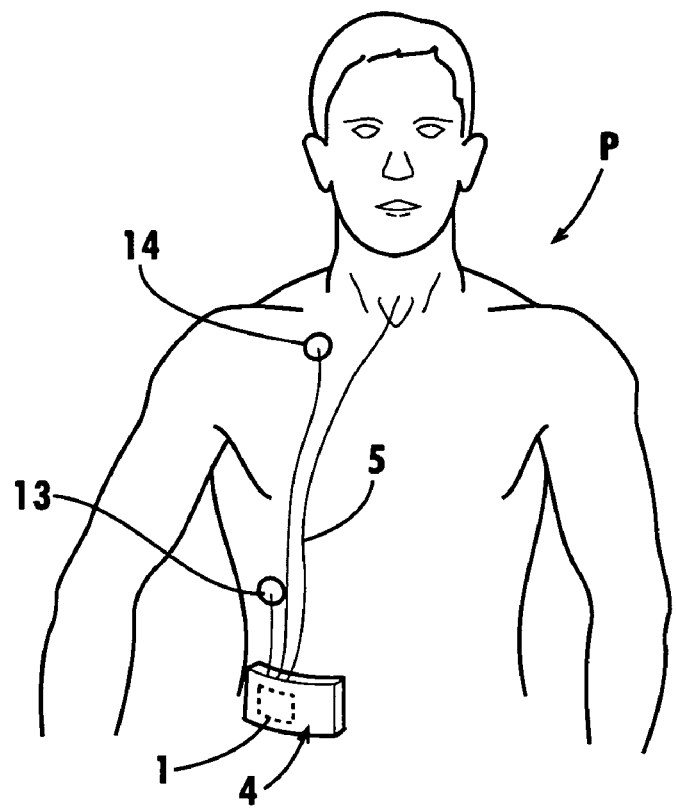
FIG. 1 shows the upper body of a patient carrying an apparatus in accordance with the invention for respiration support.

Referring specifically to FIG. 1, P designates a patient suffering from a pulmonary emphysema with an overloading and exhaustion of the respiratory pump. As a consequence, the patient can not inhale deeply enough. In addition, the exhalation process is hindered by slack and collapsing respiratory paths.

Figure 2:
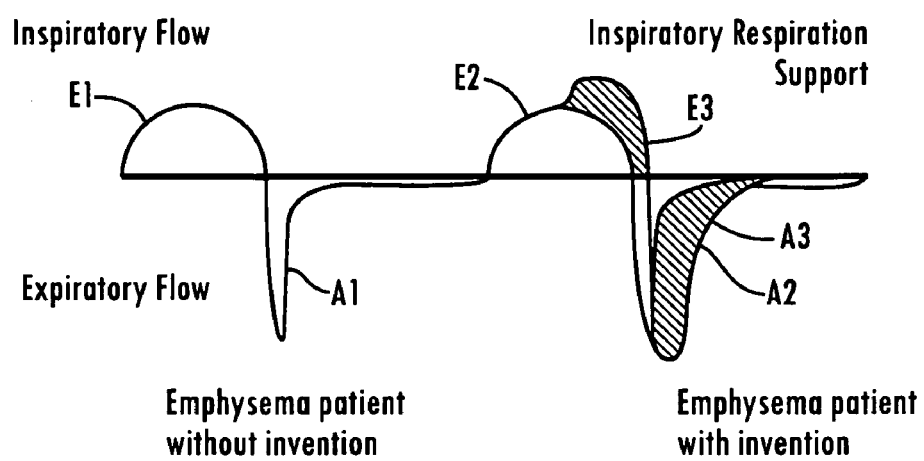
FIG. 2 shows a diagram with a view of the respiration flow of an emphysema patient with and without respiration support.

Such a respiration process with inhalation/inspiratory flow and exhalation (expiratory flow) without respiratory support is shown in FIG. 2 in the left half of the image. The curve for inhalation is designated by E1 and the curve for exhalation by A1.

In order to support and relieve the strain on the respiratory pump the patient's spontaneous respiration is detected by sensor and at the end of an inhalation process of the lungs an additional amount of oxygen is administered. This respiratory flow is illustrated in the right half of FIG. 2. The additional amount of oxygen increases the respiratory volume during inhalation according to curve E2 by the difference volume shown darkened in the upper curve and designated by E3. The additional amount of oxygen can have a volume between 25 ml and 150 ml.

In addition, the exhalation process of the patient is braked by a countercurrent. As a consequence thereof, the respiratory flow shifts during exhalation along the curved designated by A2. This purposeful resistance acting opposite to the exhalation prevents a collapsing of the respiratory paths during exhalation. In this manner the exhalation volume is increased by the volume also shown darkened and designated by A3.

As a consequence, this method avoids an insufficient respiration with an undersupply of oxygen and an increase of carbon dioxide in the blood. Patient P is significantly less stressed and more mobile and in addition he perceives less or no shortage of air.

In order to carry out the respiration support of patient P, an apparatus is provided comprising oxygen pump 1 that can be connected to an oxygen source (see FIG. 5) and comprising tracheal prosthesis 2, 3 (see FIGS. 3, 4). According to FIG. 1 oxygen pump 1 is a component of a compact, mobile respiration device 4. Oxygen pump 1 and tracheal prosthesis 2, 3 are connected via catheter 5.

As FIGS. 3, 4 show, each tracheal prosthesis 2, 3 comprises tubular support body 6 with connection 7 for catheter 5. In order to detect the spontaneous respiration of patient P two sensors 8, 9 in the form of thermistors are associated with support body 6. One sensor 8 is fixed on inner wall 10 of support body 6 and the other sensor 9 is located on outer wall 11 of support body 6. Sensors 8, 9 communicate with control unit 12 for activating oxygen pump 2. Control unit 12 is schematically shown in FIG. 5 with its inputs and outputs. As already stated, sensors 8, 9 are thermistors, that is, temperature-dependent resistors. They are connected together in a bridge circuit in the apparatus so that a compensation of measured value differences between inner sensor 8 and outer sensor takes place as a consequence of environmental influences.

FIG. 1 also shows that other respiration sensors 13, 14 are provided. They are also sensors for detecting the spontaneous respiration of patient P. An exact image of the respiration process of patient P can be obtained by adjusting the measured values received via sensors 8, 9 and 13, 14. In addition, the safety against false measurements or the failure of one of sensors 8, 9 and/or 13, 14 is increased.

In tracheal prosthesis 2 according to FIG. 3 the jet catheter 5 can be inserted via connection 7 into support body 6. End 15 of jet catheter 5 located in support body 6 is guided or deflected approximately parallel to its longitudinal axis L. The data lines from sensors 8, 9 to control unit 12 are designated with 16, 17 running inside catheter 5. On the discharge side the end 15 of jet catheter 5 is designed as jet nozzle 25. This can take place by reducing the cross section of the catheter. This increases the speed of the oxygen current at the discharge from catheter 5 and it is conducted in the direction of the bronchial tract. The diameter of support body 6 is dimensioned with a sufficiently free lumen in such a manner that patient P can freely breathe and speak even with integrated catheter 5.

Separate coupling 18 is provided on connection 7 in tracheal prosthesis 3 according to FIG. 4 via which catheter 5 is connected to tracheal prosthesis 3. In this instance fixed longitudinal section 19 aligned parallel to longitudinal axis L is provided as catheter end in support body 6 and the oxygen current is conducted via jet nozzle 26 in the direction of the bronchial tract.

Oxygen pump 1 is schematically shown in FIG. 5. It is a piston pump with double-acting piston 20 arranged in cylinder 27. The apparatus comprises four valves V1 to V4. The supply of oxygen takes place from an external oxygen reservoir via connection 21. The switching states of valves V1 to V4 and the supply lines and removal lines are designated by letters a to g.

Oxygen pump 1 functions in the apparatus during the support of respiration as follows: When valve V1 is open from c to a (b to c closed) and valve V2 open from b to e (e to d closed), piston 20 moves to the left in the plane of the figure and the oxygen flows via outlet 22 and jet catheter 5 to patient P. The additional amount of oxygen E3 is administered during the inhalation process of patient P.

When valve V1 is open from b to c (c to a closed) and valve V2 is open from e to d (b to e closed), piston 20 moves to the right in the plane of the figure in the flow of oxygen takes place in the direction of valve V3. Valve V3 is connected to the ambient air via outlet 23. In the instance in which valve V3 is open from d to g the oxygen flows off without expiration brake. That means that the exhalation process is not braked by a countercurrent.

If valve V3 is closed from d to g and open from d to f the oxygen flows via access path 24 in the direction of outlet 22 and catheter 5 in order to be administered to patient P during the exhalation process and in order to break the respiratory flow. The countercurrent prevents a collapsing of the respiratory paths and keeps them open. This makes a deeper exhalation possible.

Furthermore, valve V4 is located in access path 24 of the apparatus, via which the flow through (f to a) can be variably adjusted. This can advantageously be a proportional valve with pulse-width modulation.

Figure 6:
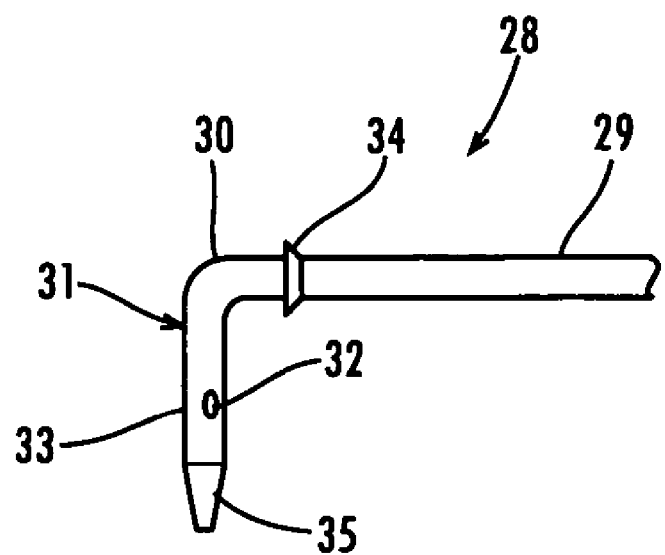
FIG. 6 shows the end section of a catheter in accordance with the invention.

FIG. 6 shows catheter 28 with long, flexible tube 29 and end 31 on the discharge side bent in curvature 30. Two sensors 32, 33 for detecting the spontaneous respiration of patient P are fastened on the end. Sensors 32, 33 are preferably thermistors. Data lines are not shown in the drawing for the sake of simplicity. They run through catheter 28 and the catheter wall. 34 designates a stop.

It can also be seen that end 31 of catheter 28 is provided with jet nozzle 35. The cross section of the flow is reduced relative to the cross section of the catheter in jet nozzle 35 so that the discharge rate of the supplied oxygen is increased.

Figure 7:
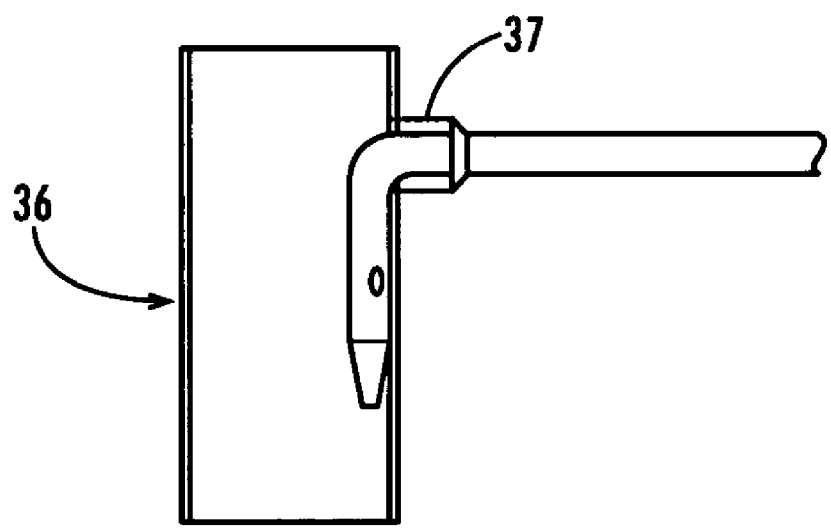
FIG. 7 shows the catheter according to FIG. 6 inserted in a support body.

Catheter 28 can be introduced into support body 36, as FIG. 7 shows. Support body 35 is located in the trachea of patient P. The connection to the outside is established via connection 37. Support body 36 can be a traditional Montgomery T-stent.

Figures 8A, 8B:
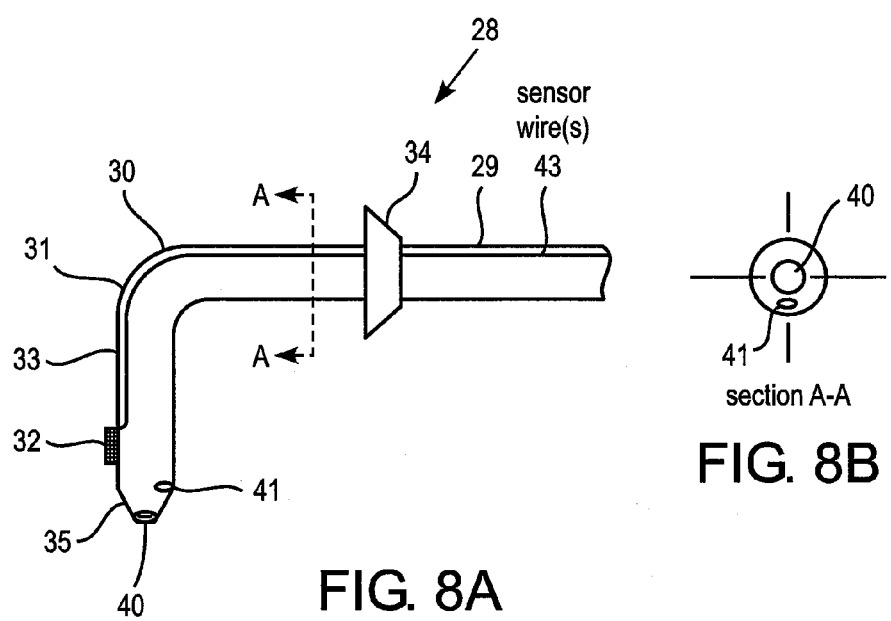
FIG. 8A shows a ventilation catheter including two lumens.
FIG. 8B shows a cross section of FIG. 8A.

FIGS. 8A and 8B show an optional embodiment in which the catheter has two lumens. Catheter 28 is shown with a first lumen 40 used for gas flow during the inhalation phase, and a second lumen 41 used for gas flow during the exhalation phase. In addition, a conducting element 43 is shown integrated into the catheter for conducting the breath sensor signal back to the control unit.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A method for supplementing respiratory volume of a spontaneously breathing patient, the method comprising:
   a) inserting a transtracheal catheter having a first end and a second end into an airway of the patient such that the second end is adapted to terminate in the trachea of the patient, wherein the inserted transtracheal catheter permits spontaneous patient breathing while inserted into the airway of the patient;
   b) determining a spontaneous inspiration process and a spontaneous expiration process of the patient; and
   c) activating a delivery mechanism based on the determining step to deliver a supplemental gas volume through the transtracheal catheter and into the patient's lungs synchronized with a portion of the patient's spontaneous inspiration process.

2. The method of claim 1, wherein the additional amount of supplemental gas volume is administered at an end of the spontaneous inspiration process.

3. The method of claim 1, wherein the supplemental gas volume is about between 25 ml-150 ml.

4. The method of claim 2, wherein the supplemental gas volume is about between 25 ml-150 ml.

5. The method of claim 1, further comprising the step of applying a countercurrent of flow into the lung in synchrony with the patient's spontaneous expiration process.

6. The method of claim 2, further comprising the step of applying a countercurrent of flow into the lung in synchrony with the patient's spontaneous expiration process.

7. An open system ventilation apparatus for supplementing respiration of a spontaneously breathing patient, comprising:
   a) a gas delivery mechanism connected to an oxygen source;
   b) a transtracheal catheter having a first end and a second end, the first end connected to the gas delivery mechanism and the second end adapted and configured for transtracheal insertion into the patient airway without obstructing the patient's spontaneous respiration phases such that the second end terminates in the trachea of the patient;
   c) at least one respiration sensor in communication with the transtracheal catheter and adapted to sense the spontaneous respiration phases of the patient; and
   d) a control unit in communication with the at least one respiration sensor, the control unit adapted and configured to control the gas delivery mechanism to deliver a supplemental volume of gas to the transtracheal catheter in synchrony with a portion of the patient's spontaneous breathing pattern.

8. The apparatus of claim 7, further comprising a tracheal prosthesis having a tubular support body, wherein the support body comprises a connection for attachment of the catheter and wherein the catheter is inserted into the tubular support body, wherein the catheter and prosthesis are designed to not occlude the tracheal airway.

9. The apparatus of claim 7, further comprising a tracheal prosthesis, wherein the sensor is associated with the tracheal prosthesis and wherein the sensor is not in line with airflow from the ventilator and not in the gas delivery circuit, and at least a portion of the sensor is in airflow in the trachea to measure spontaneous breathing airflow.

10. The apparatus of claim 7, further comprising a tracheal prosthesis having a support body, wherein the at least one sensor is coupled with an inner wall of the support body for generating a reference signal.

11. The apparatus of claim 9, wherein the second end of the catheter is located in the support body and is deflected approximately parallel to its longitudinal axis (L) and is provided on the end with a jet nozzle.

12. The apparatus of claim 10, wherein the second end of the catheter is located in the support body and is deflected approximately parallel to its longitudinal axis and is provided on the end with a jet nozzle.

13. The apparatus of claim 7, wherein the gas delivery mechanism is a piston pump, which delivers gas toward the patient when stroking in both directions.

14. The apparatus of claim 7, wherein the at least one sensor comprises at least two sensors.

15. The apparatus of claim 7, wherein the catheter has a double-lumen configuration, wherein one lumen is used for delivering the supplemental volume of gas in synchrony with the patient's spontaneous inspiratory phase of breathing and the second lumen is used for delivering the supplemental volume of gas in synchrony with the patient's spontaneous expiratory phase of breathing.

16. The apparatus of claim 7, wherein the catheter has a double-lumen configuration.

17. The apparatus of claim 7, further comprising an additional respiration sensor.

18. The apparatus of claim 7, wherein the at least one respiration sensor is adapted to be disposed on the second end of the catheter for positioning in a trachea.

19. A tracheal prosthesis comprising:
a tubular support body having a first end and a second end and a lumen therebetween, wherein the tubular support body is sized and configured to terminate within and along a portion of the trachea without occluding the tracheal airway while permitting the spontaneous breathing of a patient through the lumen;
a connector on the tubular support body between the first end and the second end, the connector configured to attach to a catheter;
a catheter having a first end and a second end and a lumen therebetween wherein the first end is connected to the connector so that the lumen of the catheter is aligned along the tubular support body lumen and toward the second end of the tubular support body; and
at least one respiration detection sensor coupled to the tubular support body, wherein the at least one respiration detection sensor is in communication with the lumen of the tubular support structure without being in line with the lumen of the catheter.

20. The tracheal prosthesis of claim 19, wherein the at least one sensor is coupled with an inner wall of the support body in the trachea.

21. The tracheal prosthesis of claim 19, wherein the connector for the catheter adapts the support body to allow the sensor to be connected to a ventilation control system.

22. The tracheal prosthesis of claim 20, wherein the sensor comprises at least two sensors, whereby a compensation of measured value difference between the sensors can be provided.

23. A catheter for delivering ventilation to a patient comprising:
an elongate body having a first end, a second end and a lumen therebetween wherein the first end is adapted and configured for connection to an outlet so that gas flowing from the outlet moves through the lumen;
the second end of the elongate body is adapted and configured for insertion transtracheally into a trachea of a patient so that the second end may be inserted into the trachea without occluding the tracheal airway of the patient such that the second end terminates in the trachea of the patient; and
at least one respiratory sensor positioned on the elongate body without being in the path of the gas flow through the lumen.

24. The catheter of claim 23, wherein a tip of the second end comprises a jet nozzle.

25. The catheter of claim 23, wherein the second end has a curved course.

26. The catheter of claims 24, wherein the second end has a curved course.

27. A method as in claim 1, further comprising the steps of: wearing the delivery mechanism utilized in the activating step so that the spontaneously breathing patient is mobile.

28. An apparatus as in claim 7, wherein the gas delivery mechanism and the control unit are configured to be worn by the spontaneously breathing patient.

29. A method of supplementing a patient's spontaneous breathing using a wearable ventilation system, the method comprising:
determining the patient's spontaneous breathing by a respiration sensor which measures intra-tracheal airflow;
delivering a supplemental volume to the patient via a transtracheal catheter having a first end and a second end that does not substantially obstruct the patient's airway and the second end is adapted to terminate in the trachea of the patient wherein the supplemental volume is delivered in synchrony with a portion of the patient's inspiratory and/or expiratory spontaneous breath phase; and
providing mobility to the patient byperforming the delivering step with the wearable ventilation system that is configured to be worn by the patient.

30. The apparatus of claim 7, wherein the catheter has a jet nozzle and the cross-section of the jet nozzle is less than the cross-section of the catheter so that a discharge rate of supplied oxygen is increased.

31. The apparatus of claim 7, wherein the sensor is a temperature dependent sensor.

32. The apparatus of claim 7, wherein the sensor comprises two thermistor sensors to compensate for measured value differences.

33. The apparatus of claim 13, further comprising a valve to control exhalation counter flow.

34. The apparatus of claim 13, further comprising at least two valves in communication with the piston pump to control gas flow delivering to the patient and recharging of the pump.

35. The apparatus of claim 7, the transtracheal catheter further comprising: a jet nozzle.

36. The apparatus of claim 7, wherein the control unit is adapted and configured to control the gas delivery mechanism to deliver the volume of gas to intermittently increase the patient's respiratory volume.

37. A tracheal prosthesis according to claim 19, wherein the catheter is a jet catheter.

38. A method according to claim 29, wherein the supplemental volume is between 25 ml and 150 ml.

39. A method according to claim 29, wherein the portion of the patient's inspiratory and/or expiratory spontaneous breath phase is an end of the inspiratory spontaneous breath phase.

* * * * *